US012745920B2

(12) United States Patent
Chevalier et al.

(10) Patent No.: US 12,745,920 B2
(45) **Date of Patent: *Sep. 29, 2026**

(54) CONNECTED IMPLANT WITH REFLECTOR

(71) Applicant: NuVasive, INC., San Diego, CA (US)

(72) Inventors: Eric Chevalier, Palaiseau (FR); Valentin Kerspern, Paris (FR)

(73) Assignee: Nuvasive, Inc., San Diego, PA (US)

( * ) Notice: Subject to any disclaimer, the term of this patent is extended or adjusted under 35 U.S.C. 154(b) by 22 days.

This patent is subject to a terminal disclaimer.

(21) Appl. No.: 18/931,260

(22) Filed: Oct. 30, 2024

(65) Prior Publication Data

US 2025/0049341 A1 Feb. 13, 2025

Related U.S. Application Data

(63) Continuation of application No. 17/784,300, filed as application No. PCT/EP2020/087253 on Dec. 18, 2020, now Pat. No. 12,150,745.

(30) Foreign Application Priority Data

Dec. 20, 2019 (EP) .................................... 19306734

(51) Int. Cl.
*A61B 5/05* (2021.01)
*A61B 5/00* (2006.01)

(52) U.S. Cl.
CPC .............. *A61B 5/05* (2013.01); *A61B 5/4504* (2013.01); *A61B 5/6878* (2013.01)

(58) Field of Classification Search
CPC ........ A61B 5/05; A61B 5/4504; A61B 5/6878
See application file for complete search history.

(56) References Cited

U.S. PATENT DOCUMENTS

2017/0143494 A1* 5/2017 Mahfouz ............ A61B 17/1703

FOREIGN PATENT DOCUMENTS

CN 102123657 A 7/2011
WO 2018195437 A1 10/2018

* cited by examiner

*Primary Examiner* — Rochelle D Turchen

(57) ABSTRACT

A system for evaluating the evolution of the structure of a subject's bone, the system including an implantable medical device including an implant body intended to be attached to the bone of the subject and at least one reflector coupled to the implant body, the reflector being configured to reflect an electromagnetic signal and being embedded in a surrounding tissue of the subject when the implant body is attached to the subject's bone and a calculation module configured to compute a parameter representative of the structure of the subject's bone, wherein the parameter is computed from a reflected signal corresponding to a reflection, on the reflector embedded in the surrounding tissue of the subject, of an excitation signal including at least one frequency in the characteristic frequency range of the reflector, the reflected signal being representative of at least one electrical property of the surrounding tissue.

11 Claims, 5 Drawing Sheets

CONNECTED IMPLANT WITH REFLECTOR

CROSS-REFERENCE TO RELATED APPLICATIONS

This patent application is a continuation of U.S. patent application Ser. No. 17/784,300 filed on Jun. 10, 2022, which is incorporated in its entirety herein.

FIELD OF THE INVENTION

The present invention pertains to the field of the implantable bone device. In particular, the present invention relates to systems and methods for evaluating the evolution of a bone structure of a subject.

BACKGROUND OF THE INVENTION

Bone regeneration is a complex, well-orchestrated physiological process of bone formation, which can be seen in particular during distraction osteogenesis, bone regeneration and normal fracture healing, and is involved in continuous remodeling throughout adult life.

The follow up of the bone regeneration to confirm the proper consolidation is commonly done using non-invasive imaging technique. Projectional radiography, using X-ray, is the most commonly used technique to evaluate the regeneration and the consolidation of bones. The image is captured by exposing the area of interest to X-rays and capturing the resulting remnant beam as a latent image. The difference between the bone and the soft tissue stems mostly from the fact that carbon has a very low X-ray cross section compared to calcium.

Also known, from application WO 2008/119992, a technique which first consists of applying and measuring alternating electrical signals emitted over a wide frequency range, within a portion of the body, then processing the electrical signals to determine the impedance and the phase shift for each of the frequencies and to use this to deduce a bone density value for that part of the body.

However, this system does not allow to obtain reliable measurements because the position of the system is not optimal. The system is not implantable, only external and mistakes can be made.

The review of the state of the art demonstrates that a need exists for an implantable system allowing the remote monitoring of bone tissue regeneration. This system would allow the subject and the practitioner to evaluate and monitor over time the local quality and the evolution of the bone tissue.

SUMMARY

The present invention relates to a system for evaluating the evolution of the structure of a bone of a subject, said system comprising:

- an implantable medical device comprising an implant body intended to be attached to the bone of the subject and at least one reflector coupled to the implant body, said reflector being configured to reflect an electromagnetic signal and being embedded in a surrounding tissue of the subject when the implant body is attached to the bone of the subject,
- a calculation module configured to compute a parameter representative of the structure of the bone of the subject, wherein said parameter is computed from a reflected signal corresponding to a reflection, on the reflector embedded in the surrounding tissue of the subject, of an excitation signal comprising at least one frequency in the characteristic frequency range of the reflector, wherein said reflected signal is correlated either directly or indirectly to at least one electrical property variation of the surrounding tissue.

The system allows to measure at least one parameter, preferably a range of parameters of the bone regeneration process for giving an indicator of the evolution of the structure of a bone to the practitioner.

In one embodiment, the system further comprises:

- an emitting module configured to emit the excitation signal comprising at least one frequency in the characteristic frequency range of the reflector;
- a receiving module configured to receive the reflected signal corresponding to a reflection of the excitation signal emitted by the emitting module on the reflector embedded in the surrounding tissue of the subject.

In one embodiment, at least two modules among the emitting module, the receiving module and the calculation module are integrated in a same external non-invasive device.

This embodiment allows to have an external noninvasive device more convenient and functional.

In one embodiment, the reflector has a plane shape or a bent shape. The different reflector shapes allow to adapt the reflector to the surface of the different implant bodies.

In one embodiment, the system comprises at least two reflectors arranged at different positions relative to the implant body. Several reflectors allow to have an accurate measure of the bone regeneration. Several reflectors on the implant body allow to monitor local information regarding to the bone quality.

In one embodiment, the calculation module is configured to compute a geometric mapping of the parameter representative of the structure of the bone of the subject from the reflected signal associated to different reflectors and their respective positions relative to the implant body.

In one embodiment, the parameter representative of the structure of the bone of the subject is computed from a comparison between the reflected signal and a model establishing a correlation between, on the one hand, a reflected signal on said reflector 3 and its surrounding tissue and, on the other hand, said parameter representative of the structure of the bone.

In one embodiment, the parameter representative of the structure of the bone of the subject is computed from a comparison between the reflected signal and a reflected signal obtained at a previous time. The comparison allows to determine the status of the bone regeneration.

In one embodiment, the implant body is an arthrodesis implant or an osteosynthesis implant. An arthrodesis implant allows to monitor the fusion between two vertebras or articulations, while, the osteosynthesis implant allows to monitor a fusion of two ends of a fractured bone.

In one embodiment, the implant body is a pin configured to be implanted into a bone to monitor an evolution of osteoporosis.

In one embodiment, the reflector is the implant body itself. The implant body is configured to emit an electromagnetic signal for monitoring the bone regeneration.

In one embodiment, the implant body comprises at least two different parts wherein at least one part comprises at least one reflector fixed onto. The first part of the implant body is an arthrodesis implant body and the second part is an implant body configured to be fixed along the spine.

The present invention also relates to a method for evaluating the evolution of the structure of a bone of a subject using an implantable medical device comprising an implant body intended to be attached to the bone of the subject and at least one reflector coupled to the implant body, said reflector being configured to reflect an electromagnetic signal and being embedded in a surrounding tissue of the subject when the implant body is attached to the bone of the subject, said method comprising steps of: emitting an excitation signal comprising at least one frequency in the characteristic frequency range of the reflector; receiving a reflected signal corresponding to a reflection of the excitation signal emitted by the emitting module on the reflector embedded in the surrounding tissue of the subject, said reflected signal being correlated either directly or indirectly to at least one electrical property of the surrounding tissue; computing, from the received reflected signal, a parameter representative of the structure of the bone of the subject.

Definitions

In the present invention, the following terms have the following meanings:

"Bone fusion" refers to the physiological of bone segments welding. The bone at the interface progressively gets denser and stiffer up to creating a rigid mechanical link between the two adjacent bone segments.

"reflector" refers to a component being configured to reflect an electromagnetic signal, and being embedded in a surrounding tissue of the subject when an implant body is attached to the bone of the subject.

DESCRIPTION OF THE DRAWINGS

The following detailed description will be better understood when read in conjunction with the drawings. For the purpose of illustrating, the system is shown in the preferred embodiments. It should be understood, however that the application is not limited to the precise arrangements, structures, features, embodiments, and aspect shown. The drawings are not drawn to scale and are not intended to limit the scope of the claims to the embodiments depicted.

Accordingly, it should be understood that where features mentioned in the appended claims are followed by reference signs, such signs are included solely for the purpose of enhancing the intelligibility of the claims and are in no way limiting on the scope of the claims.

Figure 1A:
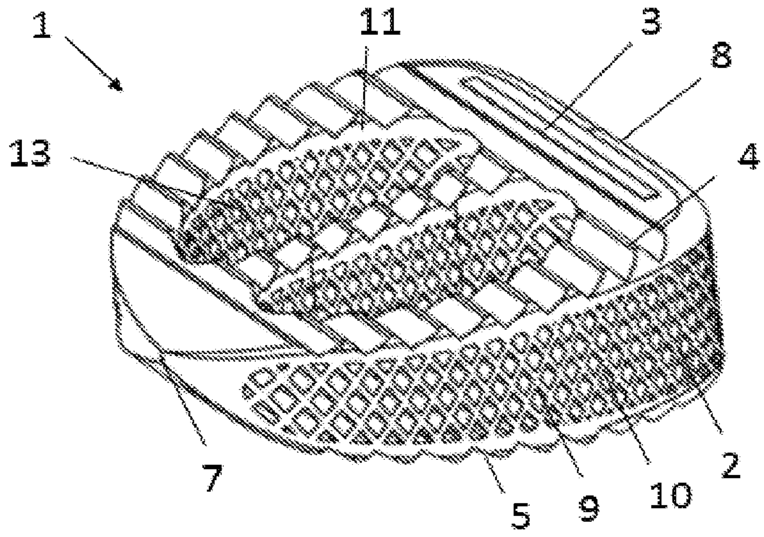

Features and advantages of the invention will become apparent from the following description of embodiments of a system, this description being given merely by way of example and with reference to the appended drawings in which:

FIG. 1*a* is a perspective view of an implantable medical device with an arthrodesis implant body and one reflector.

Figure 1B:
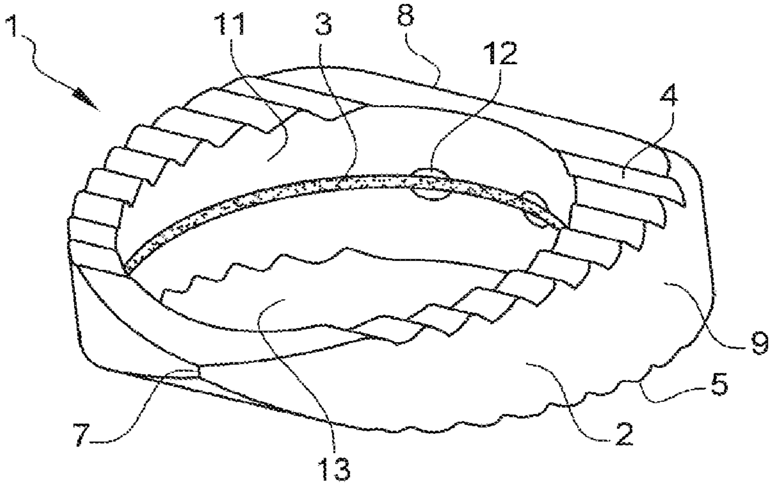

FIG. 1*b* is a perspective view of an implantable medical device with one reflector.

Figure 1C:
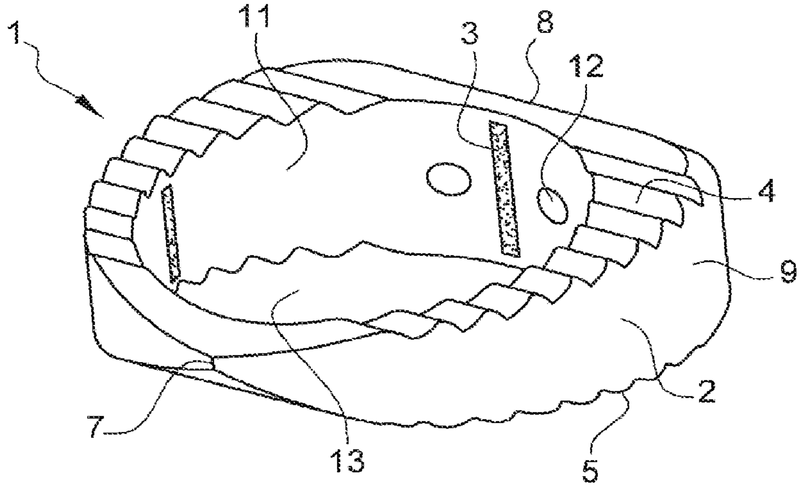

FIG. 1*c* is a perspective view of an implantable medical device with an arthrodesis implant body and several reflectors.

Figure 1D:
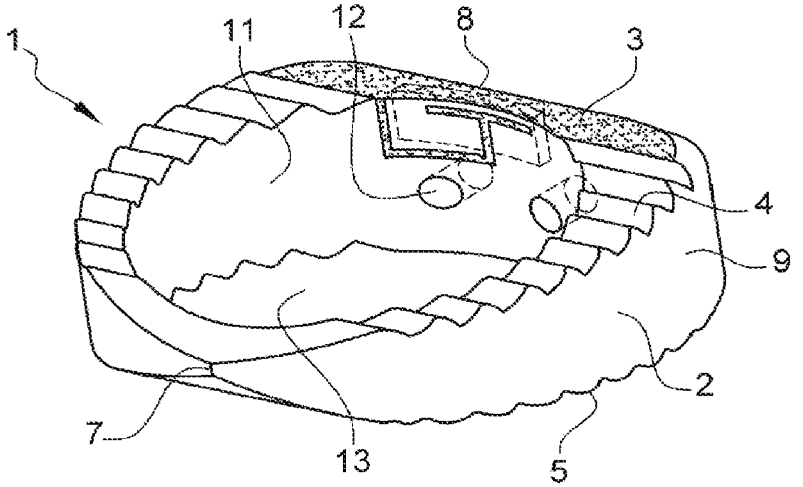

FIG. 1*d* is a perspective view of an implantable medical device wherein the reflector is in part the implant body itself.

Figure 1E:
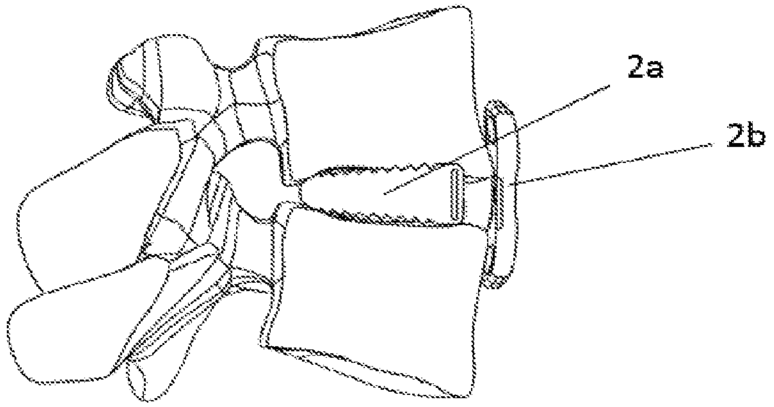

FIG. 1*e* is a perspective view of an implantable medical device with two different parts with a reflector on each part.

Figure 2A:
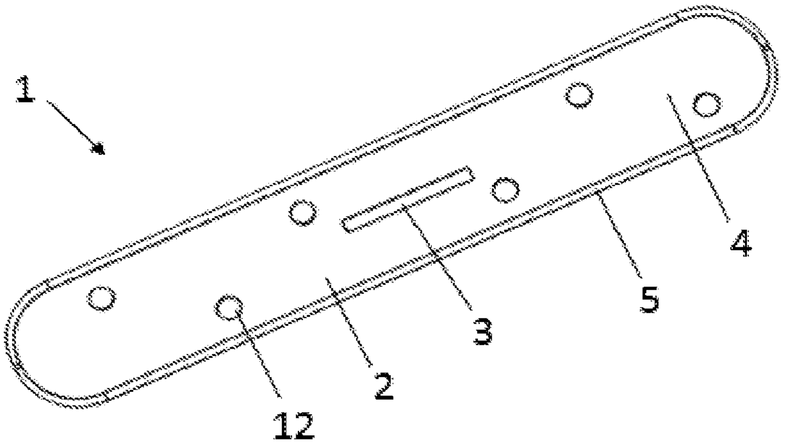

FIG. 2*a* is a first perspective view of an implantable medical device with an osteosynthesis implant body and one reflector.

Figure 2B:
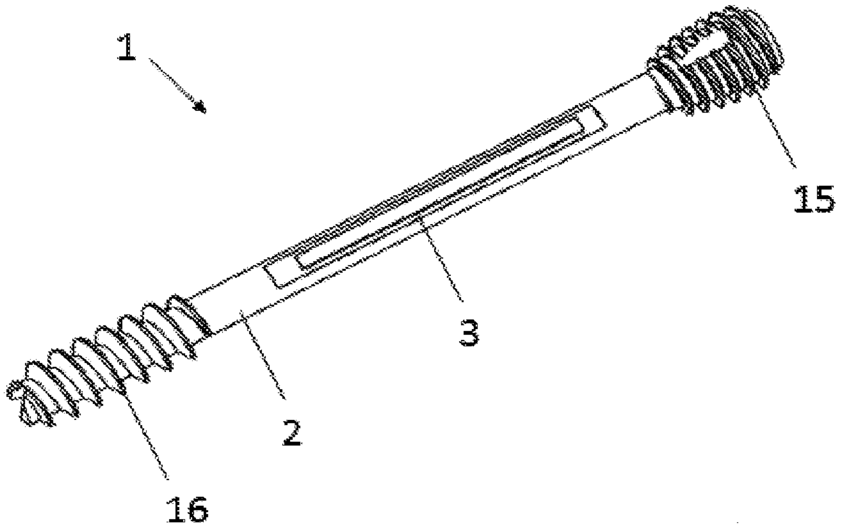

FIG. 2*b* is a first perspective view of an implantable medical device with an osteosynthesis implant body and one reflector.

Figure 2C:
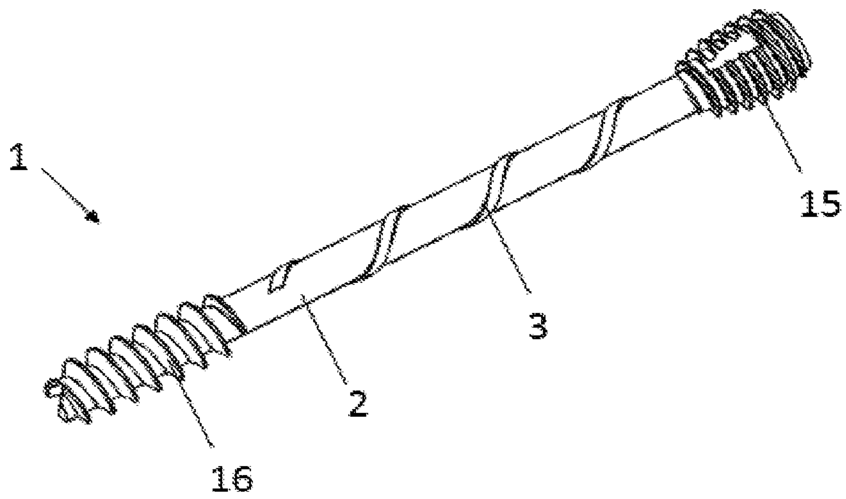

FIG. 2*c* is a second perspective view of an implantable medical device with an osteosynthesis implant body and one reflector.

Figure 3A:
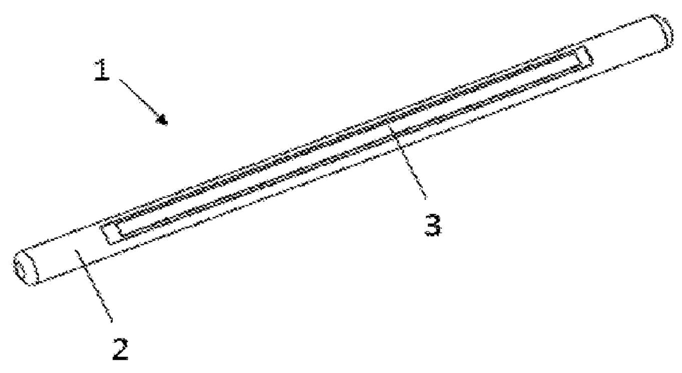

FIG. 3*a* is a first embodiment of an implantable medical device with an osteoporosis implant body and one reflector.

Figure 3B:
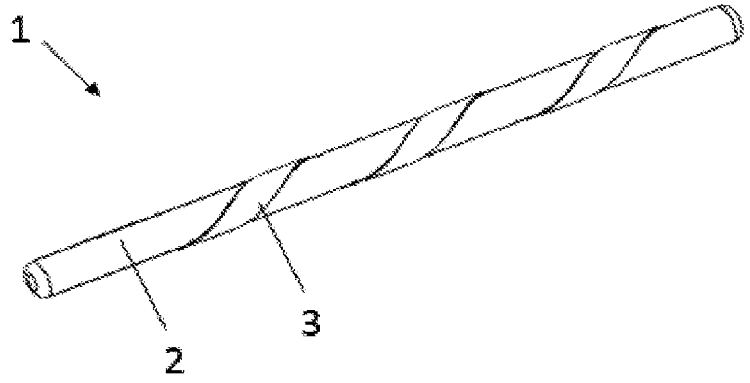

FIG. 3*b* is a second embodiment of an implantable medical device with an osteoporosis implant body and one reflector.

While various embodiments have been described and illustrated, the detailed description is not to be construed as being limited hereto. Various modifications can be made to the embodiments by those skilled in the art without departing from the true spirit and scope of the disclosure as defined by the claims.

ILLUSTRATIVE EMBODIMENTS OF THE INVENTION

The first aspect of the present invention relates to a system for evaluating the evolution of a bone of a subject, for monitoring and for confirming bone regeneration for a subject with arthrodesis. Two parameters are of great interest in the progress of the bone regeneration: the densification of the bone in the intervertebral space and the mechanical link between the adjacent vertebrae.

As shown in FIGS. 1*a* to 1*d*, a system for evaluating the evolution of the bone structure of a subject is presented. The system comprises an implantable medical device 1, said implantable medical device 1 comprising an implant body 2 and a reflector 3. In these embodiments, the implant body 2 is an interbody fusion device implanted into the spine of the subject, between two vertebras. The implantable medical device can be implanted in any part of the spine suitable to receive it. The implant body 2 may be made of various materials such as metal or polymer or ceramic for example In another embodiment, the implant body 2 may also be made of carbon graphite fiber.

The implant body 2 has an upper face 4, a lower face 5, a front face 7, a rear face 8, an external face 9 and an internal face 11. The implant body 2 has a diameter ranging from 20 to 45 centimeters. The external face 9 of the implant body 2 is smooth (FIGS. 1*b*, 1*c*, 1*d*), but in another embodiment, the external face 9 of the implant body 2 can be in a lattice structure with holes or recesses 10 on the internal 11 and/or external 9 faces of the implant body 2. Different lattice structures may be used, for example, in this embodiment, the holes or recesses 10 have a rhombus shape. In other embodiments, the shape of the holes or the recesses 10 may be rectangular, circular or other. The holes 9 are obstructed by the bone during the bone regeneration between the vertebras.

The upper 4 and lower 5 faces of the external face 9 of the implant body 2 have a stair-like shape permitting to mechanically fix the implant body 2 into the spine. The upper 4 and lower 5 faces may have a sawtooth shape or another shape. In another embodiment, the upper 4 and lower 5 faces may be rugged. In the FIGS. 1 *a* to 1 *d*, the upper 4 and lower 5 faces have the same shape. In another embodiment, the shape of the upper 4 and lower 5 faces may be different. The rear face 8 of the implant body 2 is larger than the front face 7 of the implant body. The thickness of the implant body 2 may range from 5 to 25 centimeters.

The rear face 8 of the implant body 2, comprises two cylindrical bores 12 permitting to pass the screws for fixing the implantable medical device 1 into the spine. The number of bores 12 is not limited. The bores 12 have a complementary shape with regards to its associated screws. The screws are not necessary in another embodiment. The two screw bores 12 are symmetric with respect to the reflector (FIG. 1 *c*). In another embodiment, the screw bores 12 may be placed on any part of the implantable medical device 1.

In another embodiment, the implant body 2 has no screw bores 12.

The implant body 2 is ring shaped or has a generally circular shape. The implant body 2 may have a square shape or another shape permitting to implant it into the spine. The implant body 2 has at least one internal recess 13 for allowing the regeneration of the two vertebras. In FIG. 1*a*, the implant body 2 comprises two recesses 12 while, in FIGS. 1*b* to 1*c*, the implant body 2 comprises only one recess 12. In another embodiment, the implant body 2 may be without internal recesses 13.

As presented in FIG. 1*e*, the implant body 2 may be divided in two parts 2*a* and 2*b*. The first part 2*a* is an interbody fusion device implanted into the spine of the subject, between two vertebras. The second part of the implant body 2*b* is a plate positioned on the roar of the vertebras. The second part 2*b* may have several shapes.

The implantable medical device in the FIGS. 1*a* to 1*d*, further comprises at least one reflector 3 arranged in several positions on the implant body 2 for monitoring the regeneration of the bone around the implantable medical device 1. The reflector 3 is in contact with a surrounding tissue of the subject when the implant body 2 is positioned. The at least one reflector 3 is configured to reflect an electromagnetic signal in a characteristic frequency ranging between 1 MHz and 50 GHz. Preferably, the characteristic frequency ranges between 500 MHz and 15 GHz. The reflector 3 may amplify and/or filter the reflected signal for improving the signal-noise-ratio. The number of reflectors 3 on the implant body 2 is not limited.

In the FIG. 1 *a*, a reflector 3 is positioned at the rear of the upper face 4 of the implant body 2. The reflector 3 may be placed in other positions on the implant body 2 such as the front of the upper face 4 of the implant body 2.

In the FIG. 1 *b*, a reflector 3 is located along the internal face 11 of the internal recess 13 of the implant body 2. In this embodiment, the reflector 3 is a longitudinal element extending along a longitudinal direction.

In the FIG. 1 *c*, several reflectors 3 are positioned on the internal surface 11 of the internal recess 13 of the implant body 2, one reflector 3 is positioned between the two screw's bores 12 and two reflectors 3 are positioned face each other of the internal face 11 for providing local measurement. In this embodiment, the reflectors 3 have a rectangular shape. In other embodiments, the reflectors 3 may have another shape such as a circular or a square shape. The several reflectors 3 may have different shapes for providing specific and identifiable reflected signals. The relative positions of each identifiable reflector 3 may be known at the implantation step.

In the FIG. 1 *d*, the at least one reflector 3 is in part the implant body 2 itself. The upper element 14 of the implant body 2 is configured to emit an electromagnetic wave. In another embodiment, the implant body 2 may be a reflector 3 itself. Each part of the implant body 2 may reflect an electromagnetic wave.

In another embodiment, the implant body 2 may be a reflector itself comprising at least one hole with a complementary shape of a reflector 3 permitting to reflect an electromagnetic signal without a reflector 3. In this embodiment, the implant body may be printed in 3D for example and may be made of titanium.

In the FIG. 1 *e*, at least one reflector 3 may be positioned on one of the two parts 2 *a*, 2 *b* of the implant body 2. In another embodiment, at least one reflector may be positioned on the two parts 2 *a* and 2 *b* of the implant body 2.

In another embodiment, the reflector 3 may be a passive implantable reflector and, in specific embodiments, the reflector 3 may be a resonator. For example, the resonator may be a split ring resonator or a dipole antenna.

According to one preferred embodiment, the system for evaluating the evolution of a bone further comprises a calculation module (not represented in the figures) configured to compute a parameter representative of the structure of the bone of the subject.

The emission module emits an excitation signal comprising at least one frequency, the reflector 3 receives the excitation signal in the surrounding tissue of the subject and reflects a signal to the calculation module.

The reflected signal leads to a parameter representative of the structure of the bone. After the measurement, the calculation module compares said parameter to a previous measurement. This comparison leads to an indicator of the evolution of the structure of the bone around the arthrodesis cage as presented in the FIGS. 1 *a*, 1 *b*, 1 *c*, 1 *d*, 1 *e*.

In another embodiment, the calculation module compares said parameter to a model or a predefined threshold to determine the indicator of the progress of the bone regeneration.

In an embodiment, the calculation module is a noninvasive device. In another embodiment, the calculation module may be an invasive device combined with the implantable medical device 1 for example. The parameter is computed from a reflected signal corresponding to a reflection on the reflector 3 in contact with the surrounding tissue, of an excitation signal. The reflected signal is representative of at least one electrical property such as a dielectric constant of the surrounding tissue. More precisely, the reflected signal is correlated either directly or indirectly to at least one electrical property variation of the surrounding tissue. The reflected signal can, for example, be correlated either directly or indirectly to a variation in dielectric permittivity $\varepsilon$ of the surrounding tissue. The notion of "directly" or "indirectly" refer to the possibility to correlate the reflected signal either directly to the reflected signal or, as an alternative, to a function of said reflected signal or to a parameter based on or including or depending on said reflected signal.

The dielectric parameters of the bone tissue correlated well with its composition. For example, relative permittivity at frequencies between 100 kHz and 5 MHz are different than tissue with a sparse structure. Microstructural parameters related to the surface of trabecular structure were found to be the main determinants of relative permittivity. This suggests that the When an Electromagnetic wave is incident on human tissues some of the energy is transmitted and some is reflected back, because of impedance mismatches. The reflection and transmission coefficients vary from tissue to tissue and they are dependent on permittivity, conductivity, conductivity and frequency.

A reflected electromagnetic wave is then dependent of dielectric properties of tissues; the frequency analysis of reflected electromagnetic waves leads to the detection of tissue differentiation or contrast.

When a bone tissue regeneration occurs, there is an evolution of dielectric properties which can be monitored by reflected wave analysis (in frequency or in time).

Example: Osteoporosis is a disease evolving into a severe health condition the main symptom of which is a decrease in density and a violation of the bone tissue structure.

The bone tissue generally consists of two layers: the outer layer is the cortical bone and the inner layer is the trabecular bone. When the bone tissue is damaged by osteoporosis, calcium is washed away from the trabecular bone. As a consequence, the gradually formed pores and cracks are filled with liquid components: fat and bone marrow. As a result, the development of osteoporosis leads to a change in the physical characteristics of the trabecular bone, in particular, the complex dielectric constant.

According to another embodiment, the system for evaluating the evolution of a bone comprises an emitting module configured to emit the excitation signal, the excitation signal comprising at least one frequency in the characteristic frequency range of the reflector 3.

The system also comprises a receiving module configured to receive a reflected signal; the reflected signal corresponding to a reflection of the excitation signal emitted by the emitting module on the reflector 3 in contact with the surrounding tissue of the subject. The emitting and receiving modules may be only one noninvasive device. In another embodiment, the emitting module, the receiving module and the calculation module are coupled in one noninvasive device.

In an embodiment, the noninvasive device is configured to individually identify the reflected signal of each reflector 3 of the implantable medical device 1. In another embodiment, the noninvasive device is configured to display the parameter of the progress of the bone regeneration. The parameter is computed for each reflector 3 of the implantable medical device. The advantage of this embodiment is that the practitioner may make his/her diagnosis based on the measurement provided by a specific reflector 3 located at a location of greater interest. In another embodiment, the parameter may be computed based on a synthesis of the different reflected signals of the several reflectors 3. The advantage of this embodiment is that the practitioner may make his/her diagnosis based on the set of measurements provided by each reflector 3 which represent a global information of the regeneration bone progress.

In another embodiment, the noninvasive device is configured to display the estimated time remaining before the total regeneration and formation of a bony bridge in the recess 13 of the implant. With such information the subject may adapt his/her daily life activities accordingly.

After the implantation of the implantable medical device into the spine of the subject, a process of bone regeneration is expected between the vertebras. The progress of the bone regeneration process is able to modify the excitation signal during the reflection of the reflector 3. The implantable medical device is exposed to the excitation when the practitioner uses the noninvasive device. The measurement may be made every month for example. In another embodiment, the measurement is continuous. The frequency of the measurement is not limited in times.

The measurement may be realized in two embodiments. The first embodiment is realized with a patient positioned in one position wherein each measurement is realized with a subject in the same position. The second embodiment is realized with a patient positioned in several positions wherein one measurement is realized for each position of the subject. For the second embodiment, the first measurement is realized with a subject positioned in a first position (for example, the subject would stand upright) and a second measurement is realized in a second position of the subject (for example, the subject would be bent over).

For the second embodiment, if the monitored bone has fused, no relative motion is possible, the reflected signal is unchanged between the first and the second measurements. If the monitored bone has not fused, there is a relative motion between the vertebras and the reflected signal is modified between the first and the second measurements. The direction of the shift will vary depending on the nature of the medium filling the gap. If it is blood, the frequency spectrum of the reflected signal will be shifted toward higher frequencies. If it is air, the frequency spectrum of the reflected signal will be shifted toward lower frequencies.

In another embodiment, a comparison of the shift amplitude of the reflected signal due to relative motion at several days/weeks/months interval may be measured. In this embodiment, a first and a second shift of the reflected signal are measured in the same conditions for the subject. The second shift measurement is realized for example three months after the first shift measurement. A comparison between the first and the second shift is realized, if the shift is the same, the fusion did not evolve, while, if the shift is reduced, the fusion is ongoing.

The second aspect of the present invention relates to an implantable medical device 1 for monitoring and confirming bone regeneration for a subject with osteosynthesis.

As shown in FIGS. 2 *a* to 2 *c*, the implantable medical device 1 for osteosynthesis comprises an implant body 2 divided in two parts, said two parts being one part with a plate shape and one part with threaded ends. The implantable medical device 1 for osteosynthesis also comprises a reflector 3. The implant bodies 2 are positioned on a fractured bone, more preferably on the radius, the ulna, the bones of the hand, the bones of the feet, the bones of the wrist, the bones of the face such as the mandible or the maxillary bone for example. The implant bodies 2 may be made of various materials such as metal or polymer or ceramic for example. In another embodiment, the implant bodies 2 may be made of carbon graphite fiber.

In FIG. 2 *a*, the first part of the implant body 2 is presented. The first part of the implant body 2 has an oblong shape but may be rectangular, square, circular or has another shape. In this embodiment, the first part of the implant body 2 is an osteosynthesis plate. The dimensions of the first part of the implant body 2 vary according to the fractured bone to monitor. The first part of the implant body 2 comprises bores 12 for allowing it to be screwed to the fractured bone. In the FIG. 2 *a*, the first part of the implant body 2 has six bores 12 positioned on both sides of the implant body 2. The number of bores 12 on the implant body 2 is not limited. The bores 12 are circular but may have another shape, the shape being complementary with regards to its associated screws.

Advantageously, the implantable medical device 1 is positioned on the fractured bone segments to heal. In another embodiment, the implantable medical device 1 may be fixed on every bone permitting to fix it and to monitor a fracture.

In the FIGS. 2 *b* and 2 *c*, the second part of the implant body 2 is presented. The second part of the implant body 2 is an osteosynthesis screw. The screw passes through the first part of the implant body 2, through the bores 12, crosses the fractured bone and provides information of the progress of the bone regeneration. The first part of the implant body 2 may be used with standard screws in another embodiment.

In the FIGS. 2 *b* and 2 *c*, the second part of the implant body 2 has threaded ends, allowing to insert the threaded part into the bone by screwing it directly. In this embodiment, the implant body 2 is screwed by the front end 16 of the implant body 2. The rear end 15 of the implant body 2 is threaded following the movement of the front end 16 and allowing the implantation of the implantable medical device 1. The rear end 15 has a larger diameter than the front end 16 for locking the first part of the implant body on the bone. The rear end 15 is outside the fractured bone. The rear end 15 is locked into one of the bores 12 of the first part of the implant body in this embodiment. In another embodiment, the second part of the implant body is used without the first part of the implant body for compressing the two ends of the fractured bone with each other The implantable medical device 1, in the FIGS. 2 *a* to 2 *c*, comprises at least one reflector 3 arranged in various positions on different parts of the implant body 2 for monitoring the regeneration of the fractured bone. The reflector 3 is in contact with a surrounding tissue of the subject when the different parts of the implant body 2 are positioned. The at least one reflector 3 is configured to reflect an electromagnetic signal in a characteristic frequency ranging between 1 MHz and 50 GHz. Preferably, the characteristic frequency ranges between 500 MHz and 15 GHz. The reflector 3 may amplify and/or filter the reflected signal for improving the signal-noise-ratio. The number of reflectors 3 on the implant body 2 is not limited.

In the FIG. 2 *a*, the reflector 3 is fixed on the first part of the implant body 2 at the center of the upper face 4, but in another embodiment, the reflector 3 may be in another position, for example, on the rear or front part of the upper face 4 of the implant body 2. The reflector 3 may be fixed on the upper face 4 or on the lower face 5 of the implant body 2.

In the FIGS. 2 *b* and 2 *c*, the reflector 3 is fixed on the central part of the second part of the implant body 2 The central part is not threaded but smooth. The central part may be concave, convex or plane for example. The reflector 3, in the FIG. 2 *b*, is rectangular and extends along the implant body 2. In the FIG. 2 *c*, the reflector 3 turns around the central part of the implant body 2 like a thread. The reflector 3 is made so as to fit to the shape of the central part of the implant body 2.

In other embodiments, the reflectors 3 may have other shapes such as a circular or a square shape. The several reflectors 3 may have different shapes for providing specific and identifiable reflected signals. The relative positions of each identifiable reflector 3 may be known at the implantation step.

In another embodiment, the implant body 2 may be a reflector 3 itself. Each part of the implant body 2 may be a reflector element. In another embodiment, the reflector 3 may be a passive implantable reflector and, in specific embodiments, the reflector 3 may be a resonator. For example, the resonator may be a split ring resonator or a dipole antenna. In another embodiment, the implant body 2 may be a reflector itself comprising at least one hole with a complementary shape of a reflector 3 permitting to reflect an electromagnetic signal without a reflector 3. In this embodiment, the implant body may be printed in 3D for example and may be made of titanium.

According to one preferred embodiment, the system for evaluating the evolution of a bone further comprises a calculation module (not represented in the figures) configured to compute a parameter representative of the structure of the bone of the subject.

The emission module emits an excitation signal comprising at least one frequency, the reflector 3 receives the excitation signal in the surrounding tissue of the subject and reflects a signal to the calculation module.

The reflected signal leads to a parameter representative of the structure of the bone. After the measurement, the calculation module compares the parameter to a previous measurement. This comparison leads to the evolution of the fractured bone. In another embodiment, the calculation module compares the parameter to a model or a predefined threshold to determine the progress of the bone regeneration.

In an embodiment, the calculation module is a noninvasive device. In another embodiment, the calculation module may be an invasive device combined with the implantable medical device for example. The parameter is computed from a reflected signal corresponding to a reflection on the reflector 3 in contact with the surrounding tissue, of an excitation signal. The reflected signal is representative of at least one electrical property such as a dielectric constant of the surrounding tissue. More precisely, the reflected signal is correlated either directly or indirectly to at least one electrical property variation of the surrounding tissue. This electrical property variation can be, for example, the variation in dielectric permittivity ¿.

The parameter of great interest in the progress of the bone regeneration in the osteosynthesis is the densification of the fractured bone.

According to another preferred embodiment, the system comprises an emitting module configured to emit the excitation signal, the excitation signal comprising at least one frequency in the characteristic frequency range of the reflector 3.

The system also comprises a receiving module configured to receive a reflected signal, the reflected signal corresponding to a reflection of the excitation signal emitted by the emitting module on the reflector 3 in contact with the surrounding tissue. The emitting and receiving modules may be only one noninvasive device. In another embodiment, the emitting module, the receiving module and the calculation module are coupled in one noninvasive device.

In another embodiment, the noninvasive device is configured to individually identify the reflected signal of each reflector 3 of the implant body 2. In another embodiment, the noninvasive device is configured to display a specific indicator of the progress of the bone regeneration of the fractured bone. The specific indicator is computed for each reflector 3 of the implant body 2. The advantage of this embodiment is that the practitioner may make his/her diagnosis based on the measurement provided by a specific reflector 3 located at a location of greater interest. In another embodiment, the specific indicator may be computed based on a synthesis of the different reflected signals of the several reflectors 3. The advantage of this embodiment is that the practitioner may make his/her diagnosis based on the set of measurements provided by each reflector 3 which represent a global information of the regeneration bone progress.

In another embodiment, the noninvasive device is configured to display the estimated time remaining before the total regeneration and formation of the fractured bone. With such information the subject may adapt his/her daily life activities accordingly.

After the implantation of the implantable medical device 1 on the fractured bone of the subject, a process of bone regeneration is expected between the two fractured ends of the fractured bone. The progress of the bone regeneration process is able to modify the excitation signal during the reflection of the reflector 3. The implant body 2 is exposed to the excitation when the practitioner uses the noninvasive device. The measurement may be made every month, for example. In another embodiment, the measurement is continuous. The frequency of the measurement is not limited in times.

The third aspect of the present invention relates to an implantable medical device 1 for monitoring the structure of a bone for a subject suffering of osteoporosis. The monitoring of the bone structure and composition allows the clinician to diagnose osteoporosis and to evaluate the risk of fracture encountered by the subject. Based on this information, the practitioner may be able to implement the appropriate level of treatment depending on the bone degeneration to prevent from a fracture. The invention also allows to evaluate if the medical treatment undergone by the subject for his/her osteoporotic condition provides expected outcomes and if the degeneration of the bone is slowed down. Indeed, if the treatment improves the bone quality and make it stiffer and denser.

As shown in FIGS. 3 *a* and 3 *b*, a system for evaluating the evolution of the bone structure of a subject is presented. The system comprises an implantable medical device 1, said implantable medical device 1 comprising an implant body 2 and a reflector 3. In these embodiments, the implant body 2 is an osteoporosis implant. The implantable medical device 1 may be placed on the knee, the hips, the femoral necks, the heel, the vertebrae, the wrists and the ribs for example or every bone permitting to checkup osteoporosis. The implant body 2 may be made of various materials such as metal or polymer or ceramic for example. In another embodiment, the implant body 2 also may be made of carbon graphite fiber.

The implant body 2 in the FIGS. 3 *a* and 3 *b* corresponds to a stick implant. The implant body 2 has a cylinder shape with rounded ends. The implant body 2 may have a rectangular shape or another shape with rounded ends. The implant body 2 may have spiked ends so as to facilitate the insertion of the implantable medical device 1 into the bone or the articulation to monitor.

The implantable medical device 1 in the FIGS. 3 *a* and 3 *b*, further comprises at least one reflector 3 on the implant body 2 for monitoring the status of the osteoporosis. The reflector 3 is in contact with a surrounding tissue of the subject when the implant body 2 is positioned. The at least one reflector 3 is configured to reflect an electromagnetic signal in a characteristic frequency ranging between 1 MHz and 50 GHz. Preferably, the characteristic frequency ranges between 500 MHz and 15 GHz. The reflector 3 may amplify and/or filter the reflected signal for improving the signal-noise-ratio. The number of reflectors 3 on the implant body 2 is not limited.

In the FIGS. 3 *a* and 3 *b*, the reflector 3 is located on the external surface of the implant body 2, the reflector 3 extends along the implant body 2. The central part is concave, convex or plane for example. The reflector 3, in the FIG. 3 *a*, is rectangular and extends along the implant body 2. In the FIG. 3 *b*, the reflector 3 turns around the central part of the implant body 2 like a thread. The reflector 3 is made so as to fit to the shape of the central part of the implant body 2. Several reflectors 3 may be placed on the implant body 2 for monitoring local information regarding to the bone quality.

In other embodiments, the reflectors 3 may have other shapes such as a circular or a square shape. The several reflectors 3 may have different shapes for providing specific and identifiable reflected signals. The relative positions of each identifiable reflector 3 may be known at the implantation step.

In another embodiment, the implant body 2 may be a reflector itself. Each part of the implant body 2 may be a reflector element. In another embodiment, the reflector 3 may be a passive implantable reflector and, in specific embodiments, the reflector 3 may be a resonator. For example, the resonator may be a split ring resonator or a dipole antenna. In another embodiment, the implant body 2 may be a reflector itself comprising at least one hole with a complementary shape of a reflector 3 permitting to reflect an electromagnetic signal without a reflector 3. In this embodiment, the implant body may be printed in 3D for example and may be made of titanium.

According to one preferred embodiment, the system for evaluating the quality of a bone further comprises a calculation module (not represented in the figures) configured to compute a parameter representative of the structure of the bone of the subject.

The emission module emits an excitation signal comprising at least one frequency, the reflector 3 receives the excitation signal in the surrounding tissue of the subject and reflects a signal to the calculation module.

The reflected signal leads to a parameter representative of the structure of the bone. After the measurement, the calculation module compares the parameter to a previous measurement. This comparison leads to the evolution of the bone quality. In another embodiment, the calculation module compares the parameter to a model or a predefined threshold.

In an embodiment, the calculation module is a noninvasive device. In another embodiment, the calculation module may be an invasive device combined with the implantable medical device for example. The parameter is computed from a reflected signal corresponding to a reflection on the reflector 3 in contact with the surrounding tissue, of an excitation signal. The reflected signal is representative of at least one electrical property such as a dielectric constant of the surrounding tissue. More precisely, the reflected signal is correlated either directly or indirectly to at least one electrical property variation of the surrounding tissue. This electrical property variation can be, for example, the variation in dielectric permittivity ¿.

According to another preferred embodiment, the system comprises an emitting module configured to emit the excitation signal, the excitation signal comprising at least one frequency in the characteristic frequency range of the reflector 3.

The system also comprises a receiving module configured to receive a reflected signal; the reflected signal corresponding to a reflection of the excitation signal emitted by the emitting module on the reflector 3 in contact with the surrounding tissue. The emitting and receiving modules may be only one noninvasive device. In another embodiment, the emitting module, the receiving module and the calculation module are coupled in one noninvasive device.

In another embodiment, the noninvasive device is configured to individually identify the reflected signal of each reflector 3 of the implant body 2. In another embodiment, the noninvasive device is configured to display a specific indicator of the bone quality over time. The specific indicator is computed for each reflector 3 of the implant body 2. The advantage of this embodiment is that the practitioner may make his/her diagnosis based on the measurement provided by a specific reflector 3 located at a location of greater interest. In another embodiment, the specific indicator may be computed based on a synthesis of the different reflected signals of the several reflectors 3. The advantage of this embodiment is that the practitioner may make his/her diagnosis based on the set of measurements provided by each reflector 3 which represent a global information of the bone quality.

In another embodiment, the noninvasive device is configured to display the estimated time remaining before a fracture of the bone for example. With such information the subject may adapt his/her daily life activities accordingly.

After the implantation of the implantable medical device 1 into the bone or the articulation, a process of a degeneration of the bone quality is expected. The progress of the bone degeneration process is able to modify the excitation signal during the reflection of the reflector 3. The implant body 2 is exposed to the excitation when the practitioner uses the noninvasive device. The measurement may be made every month, for example. In another embodiment, the measurement is continuous. The frequency of the measurement is not limited in times.

What is claimed is:

1. A method for stabilizing a spine comprising the steps of:

providing a spinal system:

an implantable medical device comprising an implant body intended to be attached to a bond of a subject and at least one reflector coupled to the implant body, said at least one reflector being configured to reflect an electromagnetic signal, and being embedded in a surrounding tissue of the subject when the implant body is attached to the bone of the subject, computing a parameter representative of a structure of the bone of the subject from a reflected signal corresponding to a reflection, on the at least one reflector embedded in the surrounding tissue of the subject, of an excitation signal comprising at least one frequency in a characteristic frequency range of the at least one reflector, wherein said reflected signal is correlated either directly or indirectly to at least one electrical property variation of the surrounding tissue, positioning the at least one reflector is positioned along an internal face of an internal recess of the implant body, wherein the implant body is an intervertebral implant positioned between two adjacent vertebral bodies.

2. The method according to claim 1, wherein the reflected signal is correlated either directly or indirectly to a variation in dielectric permittivity of the surrounding tissue.

3. The method according to claim 1, wherein the at least one reflector has a plane shape or a bent shape.

4. The method according to claim 1, wherein the at least one reflector comprises two reflectors arranged at different positions relative to the implant body.

5. The method according to claim 4, wherein a processor is configured to compute a geometric mapping of the parameter representative of the structure of the bone of the subject from the reflected signal associated to different reflectors of the at least one reflector and their respective positions relative to the implant body.

6. The method according to claim 1, wherein the parameter representative of the structure of the bone of the subject is computed from a comparison between the reflected signal and a model establishing a correlation between, on the one hand, the reflected signal on said at least one reflector and its surrounding tissue and, on the other hand, said parameter representative of the structure of the bone.

7. The method according to claim 1, wherein the parameter representative of the structure of the bone of the subject is computed from a comparison between the reflected signal and a reflected signal obtained at a previous time.

8. The method according to claim 1, wherein the implant body is an arthrodesis implant or an osteosynthesis implant.

9. The method according to claim 1, wherein the implant body is a pin intended to be attached to a bone to monitor an evolution of osteoporosis.

10. The method according to claim 1, wherein the at least one reflector is the implant body itself.

11. The method according to claim 1, wherein the implant body comprises at least two different parts wherein at least one part comprises the at least one reflector fixed onto.

* * * * *